United States Patent [19]

Chevigné

[11] Patent Number: 5,264,098
[45] Date of Patent: Nov. 23, 1993

[54] METHOD FOR THE SEPARATION, IDENTIFICATION AND QUANTIFICATION OF ISOENZYMES AND ISOFORMS OF ALKALINE PHOSPHATASE

[75] Inventor: Roland Chevigné, Wepion, Belgium
[73] Assignee: Analis S.A., Namur, Belgium
[21] Appl. No.: 821,411
[22] Filed: Jan. 15, 1992

[30] Foreign Application Priority Data

Jan. 15, 1991 [BE] Belgium ............................. 09100026

[51] Int. Cl.$^5$ .................... G01N 27/26; G01N 27/447
[52] U.S. Cl. ............................... 204/182.8; 204/299 R
[58] Field of Search ...................... 204/182.8, 299 R

[56] References Cited

U.S. PATENT DOCUMENTS 4,030,995  6/1977  Starkweather .................. 204/182.8

OTHER PUBLICATIONS

*Biochemical Medicine*, vol. 9, No. 3, Mar. 1974, pp. 309-315, N.Y., L. Fishman: "Acrylamide disc gel electrophoresis of alkaline phosphatase of human tissues, serum and ascites fluid using triton X-100 in the sample and the gel matrix".

*Clinical Chemistry*, vol. 28, No. 10, Oct. 1982, pp. 2007-2016, Winston-Salem, Washington, D. W. Moss et al. "Alkaline phosphatase isoenzymes".

Ari Helenius & Kai Simons "Charge shift electrophoresis: Simple method for distinguishing between amphiphilic and hydrophilic proteins in detergent solution" *Proceedings of the National Academy of Science USA* vol. 74 No. 2 (1977) 529-532.

Ole Steen Jorgensen "Charge Shift Electrophoresis of Synaptosomal Membranes Antigens" *FEBS Letters* vol. 79 No. 1 (1977) 42-44.

Michèle Granger-Schnarr et al "Specific Protein-DNA Complexes: Immunodetection of Protein Component after Gel Electrophoresis and Western Blotting" *Analytical Biochemistry* 174 (1988) 235-238.

Reinhold P. Linke, "Amphiplic Properties of the Low Molecular Weight Component of Serum Amyloid-A Protein Shown by Charge-Shift Electrophoresis" Biochimica et Biophysica Acta 668 (1984) 388-396.

Sucharit Bhakdi et al, "Detection of Amphiphilic Proteins and Peptides in Complex Mixtures, Charge-Shift Crossed Immunoelectrophoresis and Two-Dimensional Charge-Shift Electrophoresis" *Biochimica et Biophysica Acta* 470 (1977) 35-44.

Kunio Yokota et al, "Purification and characterization of amphiphilic trehalase from rabbit small intestine" *Biochimia et Biophysica Acta* 88 (1986) 405-414.

Primary Examiner—John Niebling
Assistant Examiner—John S. Starsiak, Jr.
Attorney, Agent, or Firm—Knobbe Martens Olson & Bear

[57] ABSTRACT

The invention essentially relates to a method for the separation, identification and quantification of the isoenzymes and isoforms of alkaline phosphatase in samples of physiological fluid or tissue extracts, in which method a buffer, at least one nonionic detergent and at least one anionic detergent are applied to a support medium.

Hepatic, osseous, placental, macromolecular and intestinal isoenzymes and isoenzymes bound to LpX, in particular, may be detected reliably while avoiding, as far as possible, the use of confirmation tests.

22 Claims, No Drawings

METHOD FOR THE SEPARATION, IDENTIFICATION AND QUANTIFICATION OF ISOENZYMES AND ISOFORMS OF ALKALINE PHOSPHATASE

SUBJECT OF THE INVENTION

The present invention essentially relates to an electrophoretic method permitting separation and identification of the isoenzymes and the isoforms of alkaline phosphatase present in a physiological fluid or a tissue extract.

It also relates to a densitometric method permitting quantification of the isoenzymes and the isoforms detected by the electrophoretic method of the invention.

The invention also extends to the preparations used for carrying out the method and to the products of the latter.

TECHNOLOGICAL BACKGROUND

The term alkaline phosphatase (EC3.1.3.1), abbreviated ALP, groups together a set of enzymes which, at alkaline pH, catalyze the hydrolysis of phosphoric esters.

ALP is present in the cell membranes and is found in the majority of the tissues of the body. Depending on where they are located, they will be referred to as intestinal, renal, osseous, hepatic, placental and fetal intestinal enzymes. ALP also circulate in the blood serum.

In the human body, four different genes control the expression of ALP: a non-specific tissual gene (coding for the osseous, hepatic and renal isoenzymes in particular), an intestinal gene, a placental gene and a fetal intestinal gene, each of these genes coding for a corresponding isoenzyme.

Each of these isoenzymes may undergo one or more post-translational modifications changing its physicochemical properties but preserving its biological properties and become an isoform The following isoforms are currently known: isoenzyme bound to an immunoglobulin, tetramer isoenzyme, isoenzyme having an abnormal sialic acid content, isoenzyme bound to cell membrane debris (termed macromolecular) and isoenzyme bound to a lipoprotein, for example to LpX.

The number and the amount of the various isoenzymes and isoforms of alkaline phosphatase vary very substantially depending, on the one hand, on the age and, on the other hand, on the state of health of the individuals.

The osseous and hepatic isoenzymes have been studied in particular because any primary or secondary pathology affecting the osseous and/or hepato-biliary systems is capable of causing an increase or a reduction, depending on the case, in the osseous and/or hepatic isoenzymes in the blood serum and of being accompanied by the appearance of another isoenzyme or of one or more isoforms.

It is known that the level of serum osseous isoenzymes decreases from childhood to adulthood and shows peaks at the time of surges in growth. If a child ceases to grow this is marked by an abnormal reduction in the level of osseous isoenzymes. Surges in growth are accompanied by the presence, in the blood serum, of a second osseous fraction which appears in the form of tetramers.

This fraction is absent from the serum of a normal adult, but it will be discovered if a pathological multiplication process is present in the bones (Paget's disease, osseous metastases, and the like).

An osteoclastic activity will be characterized by the presence of osseous isoenzyme having a lower sialic acid content.

The hepatic isoenzyme normally remains at a constant level throughout the life of an individual in good health.

Degenerative diseases of the liver such as fibrosis and diseases causing a hepatic infiltration and resulting in a progressive destruction of the hepatocytes result in a reduction and then in a disappearance of the hepatic isoenzyme.

An intrahepatic or extrahepatic cholostasis (hepatitis, cirrhosis, hepatic metastases and hepatic compression caused by a tumor in the vicinity, for example) may, on the other hand, cause an increase in the hepatic isoenzyme accompanied by the appearance of the isoform termed macromolecular fraction, hepato-biliary isoform or alpha 1 (bound to a membrane debris) as well as other isoforms, such as the hepatic fractions bound to various lipoproteins.

In the absence of an acute inflammation, the presence of a hepatic isoenzyme having a reduced sialic acid content is a symptom of the presence of tumor.

A hepatic isoenzyme having an abnormal sialic acid content is encountered in infantile transitory hyperphosphatasemia (viral infection of the respiratory or digestive tracts in children).

The identification of other types of isoenzymes of alkaline phosphatase also makes it possible to detect pathological disorders.

Thus, it is known that the presence of placental isoenzymes outside pregnancy is the symptom of a rapidly developing tumor pathology, that intestinal isoenzymes and isoforms in large amounts may be the mark of a systemic disease and that the fetal intestinal isoenzyme is encountered in the case of a primitive liver tumor (hepatoma).

A study of the alkaline phosphatases may therefore provide a substantial aid to diagnosis, but also in monitoring patients in order to follow the development of a disease or to objectify the effect of a treatment.

SUMMARY OF THE PRIOR ART

The various isoenzymes are customarily separated by means of electrophoresis on agarose or polyacrylamide gel or on cellulose acetate membranes.

Depending on the techniques used, some isoenzymes or isoforms are not revealed or may not be unambiguously identified. The sensitivity is also not always adequate, which prevents early detection of pathologies.

The influence of the use of nonionic detergents on the results of various types of electrophoresis is described in the literature. In the article entitled "Acrylamide disc gel electrophoresis of alkaline phosphatase of human tissues, serum and ascites fluid using triton X-100 in the sample and the gel matrix" and published in Biochemical Medicine, Vol. 9, No. 3, March 1974, pages 309-315, FISHMAN L. has shown that the use of the nonionic detergent Triton X100 in various samples and in an acrylamide gel permits the penetration into said gel of isoenzymes of high molecular weight which, in the absence of said detergent, remain at the point of application and appear as a diffuse zone.

This is confirmed in the article by MOSS et al., entitled "Alkaline phosphatase isoenzymes" and published in CLINICAL CHEMISTRY, Vol. 28, No. 10, October 1982, pages 2007-2016, Winston-Salem, Washington, US.

In the U.S. Pat. No. 4 030 995, the use of various nonionic detergents having a molecular weight of between 600 and 2000, such as Triton, Brij or Tween, has also been proposed for the electrophoresis of alkaline phosphatases on an agarose gel or a cellulose membrane. The isoenzymes penetrate into the support, improving the sensitivity but having no influence on the quality of the separation.

The anionic detergents, for their part, supply a negative charge to the various isoforms, enabling them to be spread over the entire length of the migration path. However, their use has several disadvantages: they increase the current (with the risk of rupture of the gels) and consequently the Joule effect (possible denaturing of the enzymes); these detergents additionally often have a denaturing effect at the protein (and therefore the enzyme) level and they may even be (antienzymes), that is to say cause inhibition of the phosphatase activity. Finally, they may confer too high a charge for a given isoform, causing it to migrate too strongly during electrophoresis and even to leave the gel.

If a cationic detergent is used on its own, the macromolecular fraction, the charge of which is modified, migrates in the direction opposite to that which it adopts in electrophoresis of serum proteins, which makes interpretation difficult.

For all of these reasons, the anionic or cationic detergents are hardly used in electrophoretic techniques for the identification of alkaline phosphatases.

To date, it has been possible to obtain a correct separation and a reliable identification of the osseous and hepatic isoenzymes in particular only by making use of complementary techniques involving two analyses.

Thus, it is known to carry out electrophoreses on cellulose acetate membranes by causing not only the sample to be analyzed but also a sample which has been thermally denatured for 10 minutes at 56° C. to migrate on the same support.

It is also known to treat samples with neuraminidase, which removes the sialic acid residues from alkaline phosphatases, at different speeds depending on the origin (hepatic or osseous) of the enzyme, which ensures a better separation of the electrophoretic bands corresponding to the hepatic or osseous isoenzymes. According to the known techniques, even densitometric analysis does not permit sharp detection of two separate fractions without recourse to a complementary test. It should be pointed out that neuraminidase does not act on the intestinal fraction comprising asialoglycoproteins.

The techniques involving two analyses are unfortunately slow and expensive.

The time taken for the analyses according to the known methods, including the use of a detergent, is further increased by the fact that the detergent is generally added to the gel after casting and cooling of the latter: before the electrophoresis proper it is necessary to place the gel in a buffer, termed equilibration buffer, for 30 minutes. Such buffers can be stored for only a limited time (60 days) and must therefore be replenished if analyses are carried out throughout the year.

AIMS OF THE INVENTION

The aim of the invention is to develop an electrophoretic technique which permits a correct separation of the osseous and hepatic isoenzymes of alkaline phosphatase as well as an unambiguous identification of any other isoenzyme or isoform, while having a very high sensitivity.

A further aim of the invention is to permit such a separation which may be carried out without making use of double analysis of samples.

A further aim of the invention is to provide an electrophoretic method permitting direct quantification of the osseous and hepatic isoenzymes of alkaline phosphatase in physiological fluid or tissue extracts.

A particularly valuable aim is to provide ready-for-use electrophoresis kits which can be stored for a prolonged period and which enable a good coloration of the samples to be obtained while they can be used in a simpler procedure, the duration of which is considerably reduced compared with the procedures to be applied in the known techniques.

The Applicant has found, surprisingly, that the concomitant use of nonionic detergent and anionic detergent in an agarose gel used in electrophoresis enables the above aims to be achieved.

Characteristic Features of the Invention

According to the invention, an electrophoretic method is provided for separation and identification of the isoenzymes and the isoforms of alkaline phosphatase in a sample of physiological fluid or tissue extract, in which method a buffer, at least one nonionic detergent and at least one anionic detergent are applied to the support medium. The detergents are preferably in solution in the buffer.

Preferably, each detergent is present in the buffer in an amount of 0.1 to 10 g/l.

Advantageously, the proportion between the nonionic detergent and the anionic detergent is between 1:0.5 and 2:1.

Preferably, the pH of the buffer is between 8 and 11. In a preferred embodiment, the pH is 9.45.

The buffer used is preferably tris(hydroxymethyl)aminomethane containing boric acid.

The anionic detergent may be chosen from biliary acids and biliary salts and in this case preferably comprises sodium deoxycholate or sodium taurocholate.

Alternatively, the anionic detergent may comprise a compound of formula

where $R_1$ represents a straight-chain or branched alkyl chain having 6 to 12 carbon atoms and X represents a group chosen from sulfate, sulfonate and carboxylate groups.

An amino acid derivative in which the amine group carries a N-alkyl or N-alkyl substituent having from 6 to 12 carbon atoms may also be used as anionic detergent in the method of the invention.

The support medium for the electrophoresis may be a cellulose acetate membrane, a polyacrylamide gel or an agarose gel.

In the latter case, the detergents may be added either to the buffered agarose solution, before casting the gels, or, mixed in an equilibration buffer, to the already cast gel.

The nonionic detergent is chosen from the group comprising derivatives of the Triton, Brij and Tween type, lubrol, ethylphenylpolyoxyethylene glycol and N,N-dimethyldodecylamine N-oxide.

The method of the invention may also comprise a step for quantification of the isoenzymes and the isoforms of alkaline phosphatase which have been separated and identified by said method. This quantification may be carried out by densitometric analysis at about 600 nm after incubation of the gel for 15 minutes in a solution containing 5-bromo-4-chloro-3-indolyl phosphate and nitrotetrazolium blue.

The invention also relates to kits for the electrophoresis of the isoenzymes of alkaline phosphatase, comprising an agarose gel and a detergent agent comprising at least one nonionic detergent and at least one anionic detergent. Preferably, the agarose gel in these kits is produced by introducing the detergents, dissolved in a buffer, into said gel before the solidification of the gel containing agarose.

The detergents are chosen from those mentioned above.

Another subject of the invention is an agarose gel containing said detergents.

Advantageously, the kits of the invention are produced by introducing chlorhexidine, in addition to the detergents, before solidification of the agarose. Chlorhexidine is a good preservative; one subject of the invention is its use to this end in laboratory reagents.

Another subject of the invention is the use of the kits of the invention for the identification and the quantification of isoenzymes and isoforms in samples of physiological fluid and tissue extracts.

Examples of Implementation of the Invention

The invention is illustrated by the examples of preparation of electrophoretic gels given below (Examples 1 to 4) and by a use example (Example 5).

EXAMPLES 1 TO 4 (PREPARATION)

A standard agarose solution is prepared in the following way: the following are added successively to 1 l of distilled water: 0.38 mol of tris(hydroxymethyl)aminomethane, 0.062 mol of boric acid and about 0.02 mol of sodium hydroxide to obtain a pH of 9.45. After complete dissolution, 10 g of agarose and known additives enabling the desired gel characteristics to be obtained (structure, water retention, and the like) are added, with vigorous stirring The mixture is heated to 95° C. After complete dissolution, it is cooled to 55° C.

EXAMPLE 1

1 g of ethylphenylpolyoxyethylene glycol containing 10 ethylene residues and 0.75 g of sodium N-lauroylsarcosinate and also 200 mg of chlorhexidine are added to the standard solution After complete dissolution, stirring is stopped and agarose gels (200 to 250 gels 10×7.5 cm in size) are cast on a suitable support.

EXAMPLE 2

1 g of ethylphenylpolyoxyethylene glycol containing 10 ethylene residues and 0.9 g of sodium N-lauroyl-N-methyltaurinate and also 200 mg of chlorhexidine are added to the standard solution. After complete dissolution, stirring is stopped and agarose gels (200 to 250 gels 10×7.5 cm in size) are cast on a suitable support.

EXAMPLE 3

1 g of polyoxyethylene lauryl ether, PEG 9-10 (average molecular weight 582) containing 10 ethylene residues and 0.75 g of sodium N-lauroylsarcosinate and also 200 mg of chlorhexidine are added to the standard solution. After complete dissolution, stirring is stopped and agarose gels (200 to 250 gels 10×7.5 cm in size) are cast on a suitable support.

EXAMPLE 4

1 g of N,N-dimethyldodecylamine N-oxide containing 10 ethylene residues and 0.75 g of sodium N-lauroylsarcosinate and also 200 mg of chlorhexidine are added to the standard solution. After complete dissolution, stirring is stopped and agarose gels (200 to 250 gels 10×7.5 cm in size) are cast on a suitable support.

It should be pointed out that the use of chlorhexidine (which customarily is commonly used to disinfect the hands during surgical operations or as an active disinfectant in buccal disorders, for example) as a preservative in an agarose gel is particularly advantageous: the results obtained are all equally as good as when conventionally using sodium azide, which risks forming explosive compounds in contact with metal objects, for example in water conduits.

The Applicant has successfully also used chlorhexidine for this purpose for agarose or agar gels intended for types of electrophoretic analyses other than those of the isoenzymes of alkaline phosphatase. The use of chlorhexidine as a preservative preventing the development of bacteria, molds, yeasts and algae in very diverse laboratory reagents has proved effective time and again.

EXAMPLE 5 (USE)

A gel obtained in accordance with one of the preparations described in Examples 1, 2, 3 and 4 is applied to the plate and blotted to remove excess buffer and samples are applied by a common electrophoresis method. The gel is then subjected to electrophoresis at 150 V for 25 minutes (values for a 10×7.5 cm gel), the electrophoresis buffer used preferably being a buffer identical to that used for the preparation of the standard agarose solution. After electrophoresis, the gel is incubated at 45° C. for 15 minutes with a solution of 10 ml of a 2-amino-2-methylpropanol buffer at pH 10.6 containing 5-bromo-4-chloro-3-indolyl phosphate substrate and nitrotetrazolium blue. The gel is then rinsed with distilled water and/or a 5% acetic acid solution and then dried. After rinsing, the gel may also be blotted, compressed one or more times and then dried.

It should also be pointed out that nitrotetrazolium blue amplifies the coloration obtained owing to the conversion of the substrate into a violet compound. Incubation for a quarter of an hour in the buffer is completely sufficient in order to obtain an excellent result.

After electrophoresis, the gels have a series of violet-colored bands corresponding to the various isoforms or isoenzymes contained in the samples and in the majority of cases may be identified with the naked eye.

Experimental results obtained with a large number of samples of different origin have made it possible to identify the following isoenzymes and isoforms, reliably and without recourse to a complementary analysis: isoenzymes bound to lipoproteins, isoenzyme bound to LpX, fraction X present in transitory infantile hyperphosphatasemia, the macromolecular fraction, the fetal intestinal fraction, tetramer fractions (such as the second osseous fraction, the second and the third placental fractions and the intestinal variant fraction), the hepatic fraction, the osseous fraction, the adult intestinal fraction and the hepatic, osseous and placental intestinal fractions, each of these fractions being in a form bound to an immunoglobulin.

Densitometric analysis at about 600 nm permits precise determination of the amounts of the various fractions present in a given sample. If such analyses are carried out on a given patient over a period of time, they enable the development of a disease to be followed, or a precise diagnosis to be made.

Although the above examples illustrate particularly advantageous embodiments of the invention, they in no respect restrict the scope thereof.

A mixture of nonionic detergent and anionic detergent in a buffer may also be used in electrophoresis techniques in which the support comprises cellulose acetate, for example.

In the case where, for example, a Beckman Paragon ® SPE gel is available which does not contain such a buffer containing two detergents as described above, it would not go beyond the scope of the invention to incubate a conventional gel of this type in a buffer of this type: the results obtained are entirely similar, although the procedure is longer; this type of procedure comprises an alternative which does not go beyond the scope of the invention.

I claim:

1. A method for the electrophoretic separation and identification of isoenzymes and isoforms of alkaline phosphatase in a sample of physiological fluid or tissue extract from a living organism, comprising:
   applying a buffer and at least one anionic detergent to a support medium, wherein said buffer comprises tris(hydroxymethyl)-aminomethane and boric acid;
   applying at least one nonionic detergent to said support medium;
   applying said sample to said support medium; and
   applying an electric field to said sample on said support medium to cause the separation of said sample into components.

2. The method of claim 1, wherein the anionic detergent and the nonionic detergent are applied to the support medium in the buffer.

3. The method of claim 1, wherein both the nonionic detergent and the anionic detergent are in solution in the buffer in a concentration within the range from 0.1 to 10 g/l.

4. The method of claim 1, wherein the proportion between the nonionic detergent and the anionic detergent is between 1:0.5 and 2:1.

5. The method of claim 1, wherein the pH of said buffer is between 8 and 11.

6. The method of claim 1, wherein said anionic detergent is selected from the group consisting of biliary acids and biliary salts.

7. The method of claim 6, wherein said anionic detergent is a biliary salt chosen from the group comprising sodium deoxycholate or sodium taurocholate.

8. The method claim 1, wherein said anionic detergent is a compound with the formula:

R—XNa where R represents a straight chain or branched chain alkyl group having from 6 to 12 carbon atoms and X is selected from the group consisting of sulfate, sulfonate, and carboxymethyl groups.

9. The method of claim 1, wherein the anionic detergent is an amino acid derivative N-substituted with a substituent having between 6 and 12 carbon atoms.

10. The method of claim 1, wherein said support medium comprises a cellulose acetate membrane.

11. The method of claim 1, wherein said support medium comprises a polyacrylamide gel.

12. The method of claim 1, wherein said support medium comprises an agarose gel.

13. The method of claim 12, wherein the support medium is produced according to a method comprising mixing an anionic detergent and a nonionic detergent with a buffered agarose solution and casting a gel from the mixed solution.

14. The method of claim 12, wherein the support medium is produced according to a method comprising casting an agarose gel and equilibrating said gel in buffer containing an anionic detergent and a nonionic detergent.

15. The method of claim 1, wherein said nonionic detergent is selected from the group consisting of lubrol, ethylphenylpolyoxyethylene glycol and N,N-dimethyldodecylamine N-oxide.

16. The method of claim 1, additionally comprising identifying each isoenzyme of isoform of alkaline phosphatase in said sample and quantifying the amount of each isoenzyme or isoform identified.

17. The method of claim 16, wherein the quantifying step comprises:
   incubating said support medium with a substrate containing 5-bromo-4-chloroindolyl phosphate and nitrozolium blue to produce colored bands in said support medium; and
   densitometrically analyzing said colored bands.

18. The method of claim 17, wherein the incubating step comprises 15 minutes of incubation and wherein the analyzing step comprises densitometric analysis using light at a wavelength of 600 nm.

19. A method of producing an agarose gel used for electrophoresis, comprising:
   making an agarose solution with a buffer using sufficient agarose to form a gel;
   adding at least one nonionic detergent and at least one anionic detergent to said solution;
   adding chlorohexidine to said solution; and
   solidifying said solution to form a support for the electrophoresis.

20. The method of claim 19, additionally comprising heating said agarose in solution before solidification.

21. A gel produced according to the method of claim 19.

22. An agarose gel for the electrophoresis of the isoenzymes of alkaline phosphatase comprising agarose a buffer solution, at least one nonionic detergent, at least one anionic detergent, and chlorohexidine.

* * * * *